(12) United States Patent
Maccecchini

(10) Patent No.: US 9,345,818 B2
(45) Date of Patent: May 24, 2016

(54) METHODS FOR THE IN SITU TREATMENT OF BONE CANCER

(71) Applicant: DePuy Synthes Products, LLC, Raynham, MA (US)

(72) Inventor: Maria Maccecchini, Berwyn, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 105 days.

(21) Appl. No.: 14/243,958

(22) Filed: Apr. 3, 2014

(65) Prior Publication Data

US 2014/0205648 A1 Jul. 24, 2014

Related U.S. Application Data

(60) Division of application No. 13/031,890, filed on Feb. 22, 2011, now abandoned, which is a continuation of application No. 11/418,359, filed on May 4, 2006, now Pat. No. 7,914,810.

(60) Provisional application No. 60/678,734, filed on May 6, 2005.

(51) Int. Cl.
| | |
|---|---|
| *A61F 2/28* | (2006.01) |
| *A61L 31/16* | (2006.01) |
| *A61L 27/18* | (2006.01) |
| *A61L 27/54* | (2006.01) |
| *A61L 27/58* | (2006.01) |
| *A61K 9/00* | (2006.01) |
| *A61K 31/59* | (2006.01) |
| *A61K 31/661* | (2006.01) |
| *A61K 31/675* | (2006.01) |
| *A61K 38/23* | (2006.01) |

(52) U.S. Cl.
CPC .............. *A61L 31/16* (2013.01); *A61K 9/0024* (2013.01); *A61K 31/59* (2013.01); *A61K 31/661* (2013.01); *A61K 31/675* (2013.01); *A61K 38/23* (2013.01); *A61L 27/18* (2013.01); *A61L 27/54* (2013.01); *A61L 27/58* (2013.01)

(58) Field of Classification Search
CPC ...... A61K 9/0024; A61L 27/18; A61L 27/54; A61L 27/58
See application file for complete search history.

(56) References Cited

U.S. PATENT DOCUMENTS

| | | | |
|---|---|---|---|
| 5,403,829 A | 4/1995 | Lehtinen et al. | |
| 6,221,383 B1 | 4/2001 | Miranda et al. | |
| 6,242,434 B1 | 6/2001 | Bishop et al. | |
| 6,383,190 B1 | 5/2002 | Preissman et al. | |
| 6,503,893 B2 | 1/2003 | Bishop et al. | |
| 6,548,042 B2 | 4/2003 | Arstad et al. | |
| 6,716,825 B2 | 4/2004 | Hostetler et al. | |
| 6,750,340 B2 | 6/2004 | Padioukova et al. | |
| 7,914,810 B2 | 3/2011 | Maccecchini | |
| 2004/0176327 A1 | 9/2004 | Okuno et al. | |
| 2004/0234748 A1 | 11/2004 | Stenzel | |
| 2005/0084489 A1 | 4/2005 | Wilder et al. | |
| 2006/0062825 A1 | 3/2006 | Maccecchini | |
| 2011/0142904 A1 | 6/2011 | Maccecchini | |

FOREIGN PATENT DOCUMENTS

| | | |
|---|---|---|
| JP | 03-085179 | 4/1991 |
| JP | 04-221538 | 8/1992 |
| JP | 07-313586 | 12/1995 |
| JP | 08-024347 | 1/1996 |
| JP | 09-201330 | 8/1997 |
| WO | WO 01/32100 | 5/2001 |

OTHER PUBLICATIONS

U.S. Appl. No. 60/678,734, filed May 6, 2005, Maccecchini.
European Patent Application No. 04750971.6, Communication mailed Dec. 6, 2008.
Japanese Application No. 2002-506661, Notice of the Research for the Rejection mailed Feb. 27, 2008.
Japanese Application No. 2002-506661, Official Notice of Reason for the Final Rejection mailed Jul. 11, 2008.
Kaneko et al., "Synthesis and Swelling—Deswelling Kinetics of Poly(N-Isopropylacrylamide) Hydrogels Grafted with LCST Modulated Polymers", Journal of Biomaterials Science, Polymer Edition, 1999, 10(11), 1079-1091.
Stile et al., "Synthesis and Characterization of Injectable Poly(N-Isopropylacrylamide)-Based Hydrogels That Support Tissue Formation in Vitro", Macromolecules, Nov. 1999, 32, 7370-7379.

*Primary Examiner* — Carlos Azpuru
(74) *Attorney, Agent, or Firm* — Baker & Hostetler LLP

(57) ABSTRACT

The present invention relates to methods for in situ treatment of malignant cells from a cancer associated with bone. In one method, the treatment is for a primary cancer and entails positioning an implant containing and/or coated with at least one active agent for treating malignant cells directly in/on or indirectly among/near (e.g., by placing the implant in an area immediately proximal to) a site containing the malignant cells. In another method, the treatment includes positioning an implant containing and/or coated with at least one active agent for treating malignant cells directly in/on or indirectly among/near (e.g., by placing the implant in an area immediately proximal to) a surgical site from which malignant cells were previously removed/excised.

20 Claims, No Drawings

METHODS FOR THE IN SITU TREATMENT OF BONE CANCER

CROSS-REFERENCE TO RELATED APPLICATIONS

This application is a divisional application of Ser. No. 13/031,890, filed Feb. 22, 2011, which is a continuation of application Ser. No. 11/418,359, filed May 4, 2006, which claims priority to U.S. provisional application No. 60/678,734, filed May 6, 2005, the contents of which are incorporated herein by reference in their entireties.

FIELD OF THE INVENTION

The present invention relates to methods for in situ treatment of malignant cells from a cancer associated with bone.

BACKGROUND OF THE INVENTION

Because of the tremendous impact of hyperproliferative diseases such as cancer on an ever-growing world population, there are a plethora of treatment methods that are as varied as the many different types of cancer. While general chemotherapeutic treating regimens can sometimes be effective in controlling certain types of cancer, their side effects often render them distasteful or unendurable by patients. These general chemotherapeutic treatment regimens typically take much the same form as other therapeutic/pharmaceutical delivery methods for severe illnesses, e.g., oral, intravenous, parenteral, etc. However, the fact that such delivery methods result in a widespread cellular toxicity, which is the major cause of many undesirable side effects, is a problem with conventional chemotherapy.

This down side of conventional chemotherapeutic cancer treatments can be minimized by using delivery mechanisms that specifically target cancer cells or certain hyperfunctionalities associated with malignancy, e.g., increased blood flow, increased vascularization, increased replicative function/hyperproliferation, increased selective cellular transport, etc. Many publications describe specific types of compounds (drugs) that seek out specific cells or areas having increased or decreased cellular functions specific to malignancies. Many other publications describe modified compounds, or prodrugs, in which an active compound is rendered temporarily inactive and chemically attached to a moiety (or group of moieties) designed to seek out specific cells or areas having increased or decreased cellular functions specific to malignancies, and designed to re-activate the compound at the desired time/location in vivo. Still other publications describe the use of physically sequestered compounds, e.g., time-release dosage forms, degradable drug reservoirs, pH-activated gate devices, multi-reservoir implantable chips, or the like, for treating cancer. Nevertheless, all of these methods rely on long-distance targeting, i.e., using seeker molecules that travel through the body until they find their target, only then unloading their treatment payload.

Cancers related to the skeletal system can be difficult to treat with conventional chemotherapy. For these types of cancers, an in situ treatment mechanism is needed for releasing active agents that need not be target-specific to avoid the widespread side effects of traditional chemotherapy, due to an immediate in vivo proximity to the malignant cells by virtue of in situ implantation.

Implants for treating/fixing bone injuries/deformities are well known. But because bones and orthopedic implants are essentially intermediate-term scaffolds (often load bearing, but designed to biodegrade slowly to allow bone to regrow around them/in their place), they have been utilized mostly for structural purposes. Further, while the surface characteristics of orthopedic implants have been often altered, that alteration has typically been for purposes of mechanical stability and/or biocompatibility. To the extent that there have been prior publications on active agent-loaded implantable materials, those publications have largely involved soft tissue or organs, and have largely centered on treatment of different maladies/diseases/conditions.

The present invention, as described below, offers several unique solutions to the problems and difficulties previously described.

SUMMARY OF THE INVENTION

One aspect of the invention relates to a method for in situ treatment of malignant cells from a cancer associated with bone, which includes positioning among the malignant cells an implant that at least partially chemically and/or physically associates with at least one active agent for treating the malignant cells. Advantageously, in one embodiment, the cancer associated with bone is a primary cancer.

Another aspect of the invention relates to a method for in situ treatment of malignant cells from a cancer associated with bone, which includes positioning among the malignant cells an implant that at least partially chemically and/or physically associates with at least one active agent for treating the malignant cells. In one preferred embodiment, the implant advantageously does not include a hardened bone cement within the bulk of which the at least one active agent is contained.

Another aspect of the invention relates to a medical device for in situ treatment of malignant cells from a cancer associated with bone, which contains:

a sterile, coated implant including a screw; a tack; a nail; a pin; a plate; a rod; a clamp; a staple; a spring; a stent; a suture; a membrane; a catheter; a pacemaker or other electronic device lead; a xenograft, heterograft, or allograft portion of bone, soft tissue, extracellular matrix, cartilagenous material, or a combination thereof; a composition of or containing artificial bone, demineralized bone matrix, soft tissue, extracellular matrix, cartilagenous material, or a combination thereof; a bone cement; or a combination thereof, wherein the implant at least partially chemically and/or physically associates with at least one active agent including a bisphosphonate, a monophosphonate, vitamin D and/or a vitamin D derivative, calcitonin, a statin, an anti-angiogenesis agent, an anticancer agent, an antiproliferative agent, an osteoclast inhibitor, a vasodilator, or a combination thereof.

In a preferred embodiment, the implant possesses a coating layer including a (co)polymer that contains: aliphatic ethers; aliphatic esters; alkylene esters; aromatic esters; aliphatic amides; polyamides; siloxanes; urethanes, urethaneureas, or both, having hard segments made from multifunctional isocyanates in combination with multifunctional hydroxy compounds, multifunctional amines, or both; alpha-olefins; at least partially halogenated repeat units; ionomers; hyaluronic acid and/or a salt thereof; collagen; and combinations, copolymers, or reaction products thereof, and Another aspect of the invention relates to a kit for in situ treatment of malignant cells from a cancer associated with bone, which contains:

(1) a sterile, coated implant including a screw; a tack; a nail; a pin; a plate; a rod; a clamp; a staple; a spring; a stent; a suture; a membrane; a catheter; a pacemaker or other electronic device lead; a xenograft, heterograft, or allograft portion of bone, soft tissue, extracellular matrix, cartilagenous material, or a combination thereof; a composition of or containing artificial bone, demineralized bone matrix, soft tissue, extracellular matrix, cartilagenous material, or a combination thereof; a bone cement; or a combination thereof, and (2) one or more sterile solutions, carriers, or both, each solution, carrier, or combination thereof containing at least one active agent including a bisphosphonate, a monophosphonate, vitamin D and/or a vitamin D derivative, calcitonin, a statin, an anti-angiogenesis agent, an anticancer agent, an antiproliferative agent, an osteoclast inhibitor, a vasodilator, or a combination thereof.

In one embodiment of this aspect, the implant possesses a coating layer containing: aliphatic ethers; aliphatic esters; alkylene esters; aromatic esters; aliphatic amides; polyamides; siloxanes; urethanes, urethaneureas, or both, having hard segments made from multifunctional isocyanates in combination with multifunctional hydroxy compounds, multifunctional amines, or both; alpha-olefins; at least partially halogenated repeat units; ionomers; hyaluronic acid and/or a salt thereof; collagen; and combinations, copolymers, or reaction products thereof.

These and other features and advantages of the present invention will become apparent from the remainder of the disclosure, in particular the following detailed description of the preferred embodiments, all of which illustrate by way of example the principles of the invention.

DETAILED DESCRIPTION OF THE PREFERRED EMBODIMENTS

One aspect of the present invention relates to a method of implanting a sterile, active agent-coated material and/or device for implantation into a subject. Advantageously, the method can include, but is not limited to, the following steps: providing a sterile implantable material and/or device (hereinafter "sterile implant," for convenience only and without intent to limit) that is capable of physically and/or chemically associating with an active agent; contacting the sterile implant with an active agent, e.g., by at least partially exposing the sterile implant to a preferably sterile solution containing the active agent, so that the sterile implant at least partially physically and/or chemically associates with the active agent, thus forming an active agent-loaded sterile implant; and at most a relatively short time after forming the active agent-loaded sterile implant, implanting the active agent-loaded sterile implant into a subject, e.g., an animal such as a mammal, preferably a primate or a human. For instance, see U.S. patent application Ser. No. 11/108,040 to M. Maccecchini, filed Apr. 15, 2005, and entitled "Method of Coating a Sterile, Active Agent-Coated Material and Composition Made According to Same," the entire disclosure of which is expressly incorporated by reference herein.

Before a sterile implant can be provided, typically a non-sterile implant is formed. This non-sterile implant may contain, or be made from, any suitable material, preferably a biocompatible material, and optionally but preferably a bioabsorbale, bioresorbable, and/or biodegradable material. Exemplary implant materials can include, but are not limited to: natural and/or synthetic (co)polymers; metals; metal alloys; glasses (e.g., bioactive glasses such as E-glass); metal-containing compounds such as metal oxides (e.g., ceramics), hydroxides, carbonates, nitrates, phosphates, sulfates, and the like; and combinations thereof.

The natural and/or synthetic polymers can be thermoplastic or thermoset, elastic or viscoelastic, elastomeric or non-elastomeric, semi-crystalline or amorphous, oriented or unoriented, hydrogen-bonded, or non-hydrogen-bonded, and the like, depending upon the application for which they are to be used. Natural and/or synthetic polymers can be homopolymers, blends of homopolymers, copolymers, blends of copolymers, or blends of homopolymers and copolymers. If homopolymeric, the natural and/or synthetic polymers can be, but are not limited to being, atactic, isotactic, syndiotactic, dendritic, long-chain branched/grafted, short-chain branched/hairy-rodlike, uncrosslinked, crosslinked, multi-armed stars, or the like, or some combination thereof. If copolymeric, the natural and/or synthetic polymers can include, but are not limited to, block copolymers (e.g., diblock or triblock), multiblock copolymers, long- and/or short-chain graft copolymers, long- and/or short-chain multigraft copolymers, long- and/or short-chain comb copolymers, random copolymers, alternating copolymers, heteroarmed star copolymers, diblock armed star copolymers, triblock armed star copolymers, multiblock armed star copolymers, and the like, and combinations or copolymers thereof. Copolymers according to the invention may contain two different types of repeat units or may contain more than two different types of repeat units (e.g., terpolymers contain three different types). (Co)Polymers according to the invention are preferably designated according to the process of their synthesis and not necessarily according to the end product (e.g., a completely hydrogenated polyisoprene is preferably characterized as a hydrogenated polyisoprene homopolymer and preferably not as an alternating ethylene-propylene copolymer).

Examples of natural and synthetic polymers include, but are not limited to, (co)polymers containing repeat units and/or (co)polymers made including precursors (i.e., monomers, dimers, oligomers, and the like, and combinations thereof) of aliphatic ethers (such as methylene oxide, ethylene oxide, propylene oxide, tetramethylene oxide, and the like, and copolymers and combinations thereof), aliphatic esters (such as caprolactones, e.g., $\epsilon$-caprolactone, alkylene esters, e.g., ethylene adipate, butylene adipate, ethylene succinate, ethylene sebacate, ethylene glutarate, lactides/lactic acids (such as D-, L-, D,L-, and the like, and copolymers and combinations thereof), glycolides/glycolic acids, and the like, and combinations or copolymers thereof; and the like; and copolymers and combinations thereof), aromatic esters (such as ethylene terephthalate, butylene terephthalate, isophthalates, and the like, and copolymers and combinations thereof), aliphatic amides (such as lactams, e.g., propiolactam, caprolactam, laurolactam, and the like, and combinations and copolymers thereof; polyamides, e.g., nylon 6,6, nylon 6,9, nylon, 6,10, nylon 6,12, and the like; and copolymers and combinations thereof), siloxanes (such as alkyl and/or dialkyl siloxanes, e.g., methylsiloxane, dimethylsiloxane, methylethylsiloxane, and the like, and combinations and copolymers thereof), urethanes and/or urethaneureas having hard segments made from at least diisocyanates (such as methylene diphenylene diisocyanate (MDI), methylene bis(cyclohexane isocyanate) ($H_{12}$MDI), isophorone diisocyanate (IPDI), phenylene diisocyanate, cyclohexane diisocyanate, toluene diisocyanate (TDI), methylcyclohexane diisocyanate, or the like, or combinations thereof) in combination with either diols (such as ethylene glycol, propylene glycol, butylene glycol, hexamethylene glycol, dihydroxybenzene, or the like, or a combination thereof) or diamines (such as ethylenediamine, propylenediamine, hexamethylenediamine, diaminocyclohexane, aniline, or the like, or a combination thereof) or both, optionally also including trifunctional and/or tetrafunctional components (such as triisocyanates, tetraisocyanates, triols, tetrols, triamines, tetramines, or the like, or a combination thereof) to chemically crosslink the (co)polymer system, alpha-olefins such as polyethylene (particularly UHMWPE), at least partially halogenated (particularly fluorinated) repeat units (e.g., vinyl halide, vinylidene halide, tetrahaloethylene, hexahalopropylene, perhaloalkoxy monomers such as those that form the commercial (co)polymer PFA available from DuPont of Wilmington, Del., perhaloester monomers, and the like, and combinations and copolymers thereof), ionomers (such as those that form the commercial (co)polymer SURLYN available from DuPont of Wilmington, Del., and the like), and the like, and combinations or copolymers thereof.

Metals and metal alloys useful as implant surfaces in the present invention are preferably non-toxic, preferably biocompatible, and can include, but are not limited to, titanium, chromium, manganese, cobalt, nickel, zinc, molybdenum, ruthenium, silver, tin, tantalum, gold, and the like, and combinations and alloys thereof, optionally with non-enumerated metals. In one embodiment, the metal or metal alloy can contain titanium, silver, and/or gold.

Metal-containing compounds useful as implant surfaces in the present invention are also preferably non-toxic, preferably biocompatible, and are preferably metal-containing carbides, carbonates, nitrides, nitrites, nitrates, oxides, oxynitrides, hydroxides, phosphides, phoshites, phosphates, sulfides, sulfites, sulfates, or combinations thereof. The reacted metals can include, but are not limited to, the following metals: beryllium, boron, magnesium, aluminum, calcium, titanium, vanadium, chromium, manganese, iron, cobalt, nickel, copper, zinc, strontium, zirconium, molybdenum, ruthenium, tin, barium, tantalum, and the like, and combinations thereof, optionally with non-enumerated metals. In one embodiment, the reacted metal can include one or more metals of Group IIA of the periodic table. In another embodiment, the reacted metal can include one or more of the aforementioned transition metals.

The kind of implant used in the process according to the invention is not limited and can take any appropriate form and shape desired for and/or required by the application for which it will ultimately be used. Examples of useful implants, therefore, include, but are not limited to: screws (e.g., bone screws, pedicle screws, or the like); tacks; nails (e.g., intramedullary nails, soft-tissue anchoring nails, or the like); pins (e.g., bone pins, immobilizer pins, or the like); plates (e.g., bone plates, maxillofacial plates, or the like); rods; clamps; staples; springs; stents; sutures; membranes (e.g., for protecting bones or portions thereof, for protecting osteogenic implant compositions, or the like); catheters; pacemaker or other electronic device leads; xenograft, heterograft, or allograft portions of bone, soft tissue (e.g., muscle), extracellular matrix (ECM, e.g., collagen), cartilagenous material (e.g., joints such as knee, intervertebral discs, ears, noses, or the like), or the like, or combinations thereof; compositions of or containing artificial bone, demineralized bone matrix, soft tissue (e.g., muscle), ECM (e.g., collagen), cartilagenous material (e.g., joints such as knee, intervertebral discs, ears, noses, or the like), or the like, or combinations thereof; and the like; and combinations thereof. In a preferred embodiment, the useful implant is one commercially available from Synthes (Paoli, Pa.), Stratec (Davos-Platz, Switzerland), and/or Norian (Cupertino, Calif.).

In one embodiment, the implant does not include a stent or a catheter. In another embodiment, the implant does not include a hip joint prosthesis. In another embodiment, the implant does not include a portion of soft tissue, ECM, demineralized bone matrix, or cartilagenous material, nor artificial soft tissue, ECM, or cartilagenous material. In another embodiment, the implant does not include a hardened bone cement.

Optionally but preferably (especially for implants that are non-polymeric and one or more of non-porous, non-absorbent in water or an organic liquid, and non-swellable in water or an organic liquid), the non-sterile implant is coated with a layer that is usually polymeric and/or that is one or more of porous, absorbent toward water or an organic liquid, and swellable in water or an organic liquid. The function of this coating, when present, is preferably to improve (in comparison to uncoated implants) the uptake of active agent (which is typically present in a solution of water or an organic liquid) to later form an active agent-loaded implant.

Exemplary coatings can include, but are not limited to, (co)polymers containing repeat units and/or (co)polymers made including precursors (i.e., monomers, dimers, oligomers, and the like, and combinations thereof) of aliphatic ethers (such as methylene oxide, ethylene oxide, propylene oxide, tetramethylene oxide, and the like, and copolymers and combinations thereof); aliphatic esters (such as caprolactones, e.g., ε-caprolactone); alkylene esters, e.g., ethylene adipate, butylene adipate, ethylene succinate, ethylene sebacate, ethylene glutarate, lactides/lactic acids (such as D-, L-, D,L-, and the like, and copolymers and combinations thereof), glycolides/glycolic acids, and the like, and combinations or copolymers thereof; and the like; and copolymers and combinations thereof), aromatic esters (such as ethylene terephthalate, butylene terephthalate, isophthalates, and the like, and copolymers and combinations thereof), aliphatic amides (such as lactams, e.g., propiolactam, caprolactam, laurolactam, and the like, and combinations and copolymers thereof; polyamides, e.g., nylon 6,6, nylon 6,9, nylon, 6,10, nylon 6,12, and the like; and copolymers and combinations thereof), siloxanes (such as alkyl and/or dialkyl siloxanes, e.g., methylsiloxane, dimethylsiloxane, methylethylsiloxane, and the like, and combinations and copolymers thereof), urethanes and/or urethaneureas having hard segments made from at least diisocyanates (such as methylene diphenylene diisocyanate (MDI), methylene bis(cyclohexane isocyanate) ($H_{12}$MDI), isophorone diisocyanate (IPDI), phenylene diisocyanate, cyclohexane diisocyanate, toluene diisocyanate (TDI), methylcyclohexane diisocyanate, or the like, or combinations thereof) in combination with either diols (such as ethylene glycol, propylene glycol, butylene glycol, hexamethylene glycol, dihydroxybenzene, or the like, or a combination thereof) or diamines (such as ethylenediamine, propylenediamine, hexamethylenediamine, diaminocyclohexane, aniline, or the like, or a combination thereof) or both, optionally also including trifunctional and/or tetrafunctional components (such as triisocyanates, tetraisocyanates, triols, tetrols, triamines, tetramines, or the like, or a combination thereof) to chemically crosslink the (co)polymer system, alpha-olefins such as polyethylene (particularly UHMWPE), at least partially halogenated (particularly fluorinated) repeat units (e.g., vinyl halide, vinylidene halide, tetrahaloethylene, hexahalopropylene, perhaloalkoxy monomers such as those that form the commercial (co)polymer PFA available from DuPont of Wilmington, Del., perhaloester monomers, and the like, and combinations and copolymers thereof), ionomers (such as those that form the commercial (co)polymer SURLYN available from DuPont of Wilmington, Del., and the like), and the like, and combinations or copolymers thereof. Additionally or alternately, (co)polymers that are naturally occurring (or that are synthesized to approximate those that are naturally occurring) may be useful in the coating layer according to the invention, e.g., (co)polymers containing and/ or made from hyaluronic acid and/or a salt thereof (such as lithium, sodium, potassium, magnesium, calcium, barium, or the like, or a combination thereof), collagen (such as type I, type II, or a combination thereof), or the like, or a combination thereof. In one particular embodiment, the coating layer contains or consists essentially of hyaluronic acid and/or a salt thereof (such as sodium hyaluronate). In another particular embodiment, the coating layer contains or consists essentially of a polylactic acid homopolymer or copolymer, e.g., poly(D,L-lactide), poly(D-lactic acid-co-L-lactic acid), or a combination thereof.

As is known in the art, the coating layer composition may optionally additionally include other conventional additives that may include, but are not limited to, leveling agents, various stabilizers, pH adjusting agents, defoaming agents, co-solvents, and the like, and combinations thereof, particularly if compatible with the intended use of the coated implant.

The nature of the chemical and/or physical properties of the coating can be matched to the chemical and/or physical properties of the active agent. Optionally, where the coating surface has vastly different chemical and/or physical properties than the active agent and/or active agent solution, a treatment step may be performed after the implant is coated. When performed, the treatment step includes chemically altering (e.g., functionalizing, at least partially charging, ionizing, exciting, activating, or the like, or a combination thereof) the non-sterile implant surface to attain a more hydrophilic surface and/or a surface more prone to absorb, to adsorb, and/or to retain active agent, e.g., from solution (depending upon whether the active agent is in an aqueous solution or in a solution containing an organic solvent).

If necessary to assure proper adhesion and retention of the aforementioned coating layer to the non-sterile implant, an optional treatment step may be performed before the implant is coated. The treatment step may include chemically (e.g., functionalizing, at least partially charging, ionizing, exciting, activating, or the like, or a combination thereof) and/or physically (e.g., leveling, smoothing, roughening, ablating, or the like, or a combination thereof) altering the non-sterile implant surface. Additionally or alternately, the treatment step may include applying pressure to and/or adding water and/or an organic liquid to the coated layer, e.g., to ensure as complete a contact with the implant surface as possible.

If necessary or desired during and/or after the coating step, heat and/or reduced pressure may be applied to cure and/or dry the coating layer.

The non-sterile (coated) implant can then be sterilized by any convenient sterilization process known to those in the art. Exemplary sterilization processes include, but are not limited to, the application of heat (e.g., through increasing temperature and/or through contact with a heated object such as steam, i.e., autoclaving), irradiation (e.g., with UV light, gamma rays, or the like, or combination thereof), chemicals (e.g., exposure to ethylene oxide), or the like, or some combination thereof. Once the (coated) implant is sterilized, the sterilized implant may be packaged and/or shipped for later use.

After the coating process is completed, the coated implant can also be cleaned, in addition to being sterilized. Due to the absence of any active agents on/in the coated implant, a fairly extended shelf-life can be expected.

Alternately, a pre-packaged, sterile, coated implant (e.g., containing substantially no active agents or, if containing any active agent, the active agent being of a kind and/or in an available concentration insufficient for attaining the desired therapeutic goal) may be obtained, e.g., through commercial means and may alternatively be used for convenience, instead of coating a commercially-obtained or pre-manufactured non-sterile implant.

The coating layer can be applied by any of a number of different processes known to those of skill in the art after fabrication of the non-sterile implant (e.g., by immersion or dip-coating, spray-coating, wipe-coating, injection molding, compression molding, plasma deposition, wet chemical reaction, or the like, or some combination thereof), or even during fabrication of the non-sterile implant (e.g., by co-molding, co-extrusion, simultaneous (co)polymerization, selective temperature profiling, or the like, or a combination thereof). If an appreciable amount of solvent(s) or other undesired volatile compounds is present during the coating process (e.g., in spray-coating, or particularly in dip-coating and wet chemical reaction, processes), an optional curing, or de-volatilization, step may be undertaken. Heating and/or applying a reduced pressure can help speed up de-volatilization of the solvent(s), and/or of any other volatile compounds present, in order to ensure proper setting, viscosity, hardness, and/or the like, in the coating layer. In addition, if a porous coating layer is desired, de-volatilization, e.g., by applying a combination of relatively high heat (typically not high enough to cause significant undesirable oxidation or degradation in either the coating layer or the underlying non-sterile implant, or both) with a relatively high vacuum (e.g., the combination of reduced pressure and the increased temperature can allow sufficient volatilization of the solvent(s) and/or of any other volatile compound(s) present so as to encourage those compounds to boil relatively rapidly and thus to cause pockets/bubbles of escaping gas to form; by adjusting the viscosity, hardness, and/or (co)polymer fraction in the coating layer, the bubbles can be induced to coalesce to provide a certain level of porosity in the coating layer). Although the combination of relatively high heat with a relatively high vacuum can generally result in a highly non-uniform coating layer and/or coating layer outer surface, such non-uniformity may be an acceptable effect of obtaining a porous coating.

It is noted that, in certain cases, it may not be desirable to coat the entire surface of the non-sterile implant. For example, for implants that may typically encounter significant and/or repetitive shear and/or frictional stresses, but typically not those that encounter only extensional and/or compressive stresses, such that a coating layer would quickly delaminate or be worn away and thus would be of little practical value. Such circumstances may typically arise in, but are in no way limited to, the context of artificial joints or portions thereof; invertebral spinal discs; artificial muscles or portions thereof; springs; the legs of a staple or the end of a tack, nail, or pin that are driven into bone; the threading of a screw that is twisted into bone; and the like. In such circumstances, the coating layer may optionally be applied only to a selected portion of the implant (e.g., to the portion of the implant that preferably does not encounter significant and/or repetitive shear and/or frictional stresses).

The thickness of the coating layer is not necessarily constrained, nor is the thickness necessarily uniform on all portions of the implant (which are coated—the uncoated regions of the implant, if any, are specifically excluded from this uniformity consideration). Indeed, the coating layer (or the surface layer of the implant itself, if uncoated) is preferably thick enough to allow and/or facilitate physical and/or chemical association between the coating layer and the active agent (or the active agent-containing solution). Thus, in one embodiment, the average thickness of the coating region is from about 10 nm to about 1 mm, depending upon the application for which the coated implant is to be used. In embodiments where a relatively thin coating layer is desired, the average thickness can be less than about 1000 nm, alternately from about 10 nm to about 1000 nm, from about 20 nm to about 500 nm, from about 10 nm to about 250 nm, from about 100 nm to about 1000 nm, or from about 250 nm to about 800 nm. In embodiments where a relatively thick coating layer is desired, the average thickness is from about 1 micron to about 1000 microns, alternately from about 1 micron to about 500 microns, from about 2 microns to about 300 microns, from about 5 microns to about 500 microns, from about 10 microns to about 800 microns, from about 50 microns to about 750 microns, or from about 250 microns to about 900 microns.

By loading the active agent into/onto/within the implant coating, the active agent can thereby be concentrated where it is most needed in vivo, while its presence, and consequently its effect, throughout the rest of the body can thus be minimized. An "active agent," as used herein, should be understood to mean an agent that exhibits or can be caused to exhibit a therapeutically or diagnostically beneficial effect in the body.

The active agent (while the term "active agent" is referred to in its singular form, without any intent to limit, it should be understood that this term refers equally to mixtures and/or complexes of multiple active agents, which are also considered to be part of the present invention) may be chemically and/or physically associated with the coating layer (or with the surface of the sterilized implant, if no separately added coating layer is desired or necessary) using any number of means known to those of skill in the art. Indeed, the active agent may be contacted with the coating layer by means similar to those used to deposit the coating layer (e.g., immersion or dip-coating, spray-coating, wipe-coating, wet chemical reaction, or the like, or some combination thereof). While the pure active agent itself is typically a liquid or a solid between about room temperature (let's say about 15° C.) and about human body temperature (about 37° C.), an advantage may be obtained by placing or obtaining the active agent in an acceptable carrier/solution (hereinafter "solution," for convenience only and without intent to limit). The solution need not completely dissolve the active agent (although that may be desired in some embodiments of the present invention), but generally should sufficiently attain a viscosity sufficient to allow the active agent to physically and/or chemically associate with the coating layer (e.g., in some embodiments, a more viscous solution may be desired so as to attain a thicker coating such as in an immersion or dip-coating process; in other embodiments, a less viscous solution may be desired so as to attain a thinner coating such as in an immersion or dip-coating process or so as to attain better flow such as through the tubes/pipes of a spray-coating apparatus). Thus, precipitated solutions, colloidal solutions, suspensions, emulsions, latices, flocculated solutions, agglomerated solutions, supersaturated solutions, and the like can be acceptable substitutes for substantially and/or completely dissolved active agent solutions.

There are many potential active agent categories for loading in/on the (coating layer of the) implants according to the present invention. Which category of active agents, and in fact which particular active agent, to employ will typically depend upon the goal to be attained by the active agent and optionally but preferably also upon the application for which the implant is to be used. For instance, where the implant is associated with a bone injury (e.g., bone screw, bone plate, a bone replacement composition, a protective membrane for bone replacement composition, or the like), a useful active agent may include an osseointegrative, osteoconductive, and/or osteoinductive agent (such as a morphogenic protein, a mito-genic protein, or a combination thereof), an antibacterial compound, an angiogenesis agent, an antiinflammatory agent, a nutrient, or the like, or a combination thereof, optionally depending upon a particular patient or surgical need. A non-exclusive list of active agents follows: antibacterials, antivirals, antimicrobials, angiogenesis agents, antiinflammatories, anticancer agents, antiproliferative agents, anticlotting agents, antioxidants, antifungals, analgesics, antiseptics, bioabsorbability/bioresorbability enhancers, bisphosphonates, calcitonins, chemotherapeutics, clotting agents, drugs for treating pain, immune system boosters, immunosuppressants, immunomodulators, nutrients (e.g., vitamins), osteoclast inhibitors, osteoconductors, osteoinductors, osseointegrative agents, statins, vasodilators, vasoconstrictors, salts thereof (where applicable), and combinations thereof. Other additionally or alternately acceptable active agents and active agent categories can be found, e.g., in U.S. Pat. No. 6,221,383, the disclosure of which is hereby incorporated by reference.

In a preferred embodiment, the at least one active agent contains or consists essentially of a bisphosphonate, a monophosphonate (e.g., such as described in U.S. Pat. No. 6,716,825, the contents of which are incorporated herein by reference), vitamin D and/or a vitamin D derivative/analog (e.g., such as described in U.S. Pat. Nos. 6,503,893 and 6,242,434, the contents of each of which are incorporated herein by reference), calcitonin, a statin, or a combination thereof. In another preferred embodiment, the active agent contains or consists essentially of an anti-angiogenesis agent, an anticancer agent, an antiproliferative agent, an osteoclast inhibitor, a vasodilator, or a combination thereof. As used herein, when used to precede element(s) of the invention, the articles "a" and "an" should be understood to mean one or more of the element(s), and not merely a single one of the element(s).

Bisphosphonate compounds useful in the present invention should be understood to encompass the acid form of the compounds, as well as partially- and/or fully-substituted salt and/or ester forms of the compounds, while alternately or additionally including partially and/or fully hydrated forms of the compounds. Examples of bisphosphonates according to the invention include, but are not limited to, etidronate (e.g., commercially available under the tradename DIDRONEL™), clodronate/clodrinate (e.g., commercially available in its disodium salt form from Leiras Oy under the tradename BONEFOS™), pamidronate (e.g., commercially available under the tradename AREDIA™), alendronate (e.g., commercially available in its sodium salt form from Merck under the tradename FOSAMAX™), olpadronate, amino-olpadronate, ibandronate, neridronate, nedrinate, medronate, tiludronate (e.g., commercially available from Sanofi under the tradename SKELID™), risedronate (e.g., commercially available from Proctor & Gamble under the tradename ACTONEL™), zolendronate (e.g., commercially available in its acid form under the tradename ZOMETA™), EB-1053, YM-175, CGP 42'446, YM 529, U-81581, FR-78844, BM-21.0955, those bisphosphonates and/or bisphosphinic acid derivatives described in Published U.S. Patent Application No. US 2004/0176327 A1, those bisphosphonates and/or bisphosphinic acid derivatives described in U.S. Pat. No. 5,403,829, those bisphosphonates and/or bisphosphinic acid derivatives described in U.S. Pat. No. 6,548,042, those bisphosphonates and/or bisphosphinic acid derivatives described in U.S. Pat. No. 6,750,340, and the like, and combinations thereof.

In other embodiments, the active agent can include an antibacterial agent, an antiviral agent, an osseointegrative, osteoconductive, and/or osteoinductive agent, or a combination thereof. In another embodiment, the active agent can contain or may consist essentially of mitogenic growth factors such as IGF and/or PDGF, morphogenic growth factors such as TGF and/or BMP, osteoclast inhibitors such as calcitonin and/or bisphosphonates, antiinflammatories, and any combination thereof.

In the embodiment of the coating of the invention having a therapeutic or diagnostic agent bound to the medical device surface, directly or via a linking agent, the coating of the invention can advantageously provide localized delivery of the therapeutic or diagnostic agent. Similarly, the coating of the invention can also improve the residence time of the therapeutic or diagnostic agent. By binding the agent to the device, the rapid clearance from the bloodstream of the therapeutic or diagnostic agent, as for example when the body's immune system phagocytizes the therapeutic agent or a liposome containing the agent, can be avoided.

In one embodiment of the invention, release of the therapeutic or diagnostic agent within the patient from the medical device surface is provided by the coating of the invention. Such release of the therapeutic agent from the device surface may be desirable as occurring over a viable dosage period, e.g., a time release or extended release formulation.

In an alternate embodiment, the therapeutic or diagnostic agent can include, but is not limited to: proteins; peptides; oligonucleotides; antisense oligonucleotides; cellular adhesion promoting proteins or peptides including extracellular matrix proteins; polysaccharides such as heparin, hirudin, hyaluronan, and chondroitin; nitric oxide donating compounds; vascular growth factors such as VEGF; antitumor agents such as Taxol, Paclitaxel, Carboplatin, and Cisplaten; and analogs, derivatives, and mixtures thereof. For example, paclitaxel (taxol) derivatives that may be suitable for use in the present invention can include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

Active agent carriers typically have some interaction with the active agent and can serve to dilute the concentration of the active agent, if desired, but generally do not affect the therapeutic and/or diagnostic effectiveness of the active agent in vivo. However, active agent carriers may optionally facilitate association of the active agent with the coated implant surface, e.g., through a physical and/or chemical association both with the active agent and with the coated implant surface. Carriers, as used herein, include, but are not limited to, adjuvants, excipients, solutions, emulsions, suspensions, colloidal phases, slurries, encapsulants, or the like, or a combination thereof. For example, where an extended dosage time and/or a time release formulation is desired, the active agent can be present in a first phase that is encapsulated by a second phase (e.g., water-in-oil-in-water emulsions, oil-in-water-in-oil emulsions, microsphere encapsulation, micelle encapsulation, or the like, or a combination thereof.

Examples of active agent carriers can include, but are not limited to, water, saline, buffered aqueous solutions, supercritical carbon dioxide, polar organic solvents, non-polar organic solvents, and the like, and combinations thereof. In one preferred embodiment, the active agent can be present in a solution or slurry containing water.

Polar organic solvents include, but are not limited to: alcohols such as ethanol, propanol, isopropanol, and the like; alkylene glycols such as ethylene glycol, oligomeric poly (ethylene oxide) glycols, butanediol, and the like; multiply hydroxy-functional compounds such as glycerol and the like; aldehydes such as acetaldehyde, formaldehyde, and the like; ketones such as acetone, methyl ethyl ketone, methyl isobutyl ketone, and the like; amines such as mono-, di-, and/or tri-substituted alkylamines; amides such as dimethylformamide, dimethylacetamide, formamide, acetamide, acrylamide, and the like; carboxylic acid-functional compounds such as acetic acid, citric acid, and the like, as well as salts and/or esters thereof; halogenated hydrocarbons such as chloroform, methylene chloride, trichloroethane, bromoform, and the like, but preferably excluding chlorofluorocarbons and perhalohydrocarbons and optionally excluding halogenated aromatic compounds; sulfur-containing compounds such as dimethylsulfoxide and the like; fatty acids such as oleic acid, stearic acid, linoleic acid, behenic acid, palmitin acid, myristic acid, caproic acid, caprylic acid, capric acid, lauric acid, palmitoleic acid, and the like, as well as esters thereof such as diglycerides, triglycerides, and the like; natural or synthetic oils such as corn oil, canola oil, olive oil, sunflower oil, safflower oil, flaxseed oil, grapeseed oil, rapeseed oil, cottonseed oil, linseed oil, sesame oil, peanut oil, and the like; compounds containing more than one type of polar functional group enumerated herein such as citric acid; and the like; and combinations thereof.

Non-polar organic solvents include, but are not limited to: straight or branched alkanes such as pentane, hexanes, decanes, dodecanes, mineral spirits, oligomeric poly(alpha-olefin)s, and the like; cyclic alkanes such as cyclohexane and the like; straight or branched alkenes such as hexenes, butadiene, hexadiene, octadiene, septatriene, octatriene, and the like; cyclic alkenes such as cyclohexadiene, cyclooctatriene, norbornene, and the like; and the like; and combinations thereof.

When present with a carrier, the relative concentration of active agent in solution can advantageously be sufficient to permit and/or facilitate adsorption by, absorption into, uptake by, and/or bonding with the coating layer (and/or the exposed surface layer of the implant). Such active agent concentration can be expressed in weight percentage terms (e.g., from about 0.01% to about 75%, from about 0.1% to about 50%, from about 0.05% to about 20%, from about 0.2% to about 10%, from about 0.5% to about 25%, from about 0.05% to about 5%, or from about 1% to about 40%) or can alternately be expressed in terms of molarity (e.g., from about 0.0001M to about 5M, from about 0.001M to about 2M, from about 0.0005M to about 1M, from about 0.01M to about 0.7M, from about 0.05M to about 1.5M, from about 0.001M to about 0.5M, or from about 0.1M to about 3M), based on the solution/carrier composition, separate from the implant.

Any methods known to those of skill in the art for sterilizing solutions can be utilized in the method according to the present invention. One preferred example of sterilizing a solution includes filtering the solution through an appropriate filter/filtration apparatus (e.g., containing a filter having pore sizes not larger than about 0.45 microns, alternately not larger than about 0.22 microns, which are widely available commercially through a variety of sources). This liquid-based filtration method typically requires that the viscosity of the solution be manageable so that the pressure necessary (if any) to allow the solution to pass through the filter and/or requires that the active agent be sufficiently soluble in the solution so that any active agent-related solids therein have a diameter no larger than about the maximum pore size of the filter.

In addition, it is noted that the vessel in which the active agent-containing solution is held must also be sterilized to assure that the active agent-containing solution remains sterile throughout the method according to the invention. Similarly, in a process using an apparatus, each of the components of the apparatus must also be sterilized to assure that the active agent-containing solution remains sterile throughout the method according to the invention. These sterilization processes can be performed using any of the appropriate sterilization techniques described herein and/or known to those of skill in the art.

The active agent (and its optional carrier) can be handled separately in a vessel, for instance, according to general methods with which doctors and hospitals are acquainted. Just prior to implantation, the sterile coated implant can, in one embodiment, be immersed in the vessel in order to allow the coating layer of the implant to chemically and/or physically associate with the active agent and/or the active agent solution.

The active agent loading level (as well as the loading level of the solvent/carrier, if desired) in/on the implant can be easily and precisely adjusted by controlling the concentration of the active agent (and optionally the solvent/carrier concentration as well) in the solution, by carefully choosing the chemical nature of the solvent/carrier with an eye toward its compatibility or incompatibility with the coating layer material/surface, and/or by controlling the coating layer exposure time thereto.

The active agent loading level in/on the implant (coating layer) can advantageously be sufficient to permit, facilitate, catalyze, and/or encourage the expression of the desired active agent effect(s) and/or the attainment of the desired therapeutic/diagnostic result(s) in vivo when implanted in a subject. Similarly, if the solvent/carrier, independently or in conjunction with the active agent, permits, facilitates, catalyzes, and/or encourages the expression of the desired active agent effect(s) and/or the attainment of the desired therapeutic/diagnostic result(s) in vivo, then its concentration within the implant (coating layer) may be controlled as well.

In one embodiment, where it is desired that two or more active agents be incorporated into/loaded onto the implant, there may be difficulty in combining and/or solublizing the two or more active agents in a single solution/carrier composition. In such an embodiment, the two or more active agents may be separated into multiple solutions/carriers in multiple vessels, each vessel containing a solution/carrier composition containing an individual active agent or a soluble/compatible combination of active agents. In such an embodiment, the sterile coated implant can, e.g., be successively immersed in each of the vessels in order to allow the coating layer of the implant to chemically and/or physically associate with the respective active agents and/or the active agent solutions. In an alternate embodiment, e.g., where the two or more active agents cannot effectively be loaded into the same portion of the coating layer, steps may be taken to load different portions of the coating layer (whether they be radially uniform and separated by depth from the coating layer surface, or whether they be radially distinct and separated into distinct, e.g., circumferentially-spaced, sections containing the different active agents) with different (sets of) active agent(s).

Once sufficiently loaded with active agent, the implant can subsequently be maneuvered into position within a patient and (optionally permanently) implanted. In one embodiment, the method according to the present invention includes substantially contemporaneously loading the sterile, coated implant with an active agent and implanting the sterile, coated, active agent-loaded implant into a subject. "Substantially contemporaneously," as used herein, should be understood to mean that the step of loading the sterile, coated implant with an active agent occurs at a time from immediately before to a reasonable time before implanting the sterile, coated, active agent-loaded implant into a subject. In one embodiment, the time between forming the active agent-loaded sterile implant and implanting the active agent-loaded sterile implant into a subject can be from about 20 seconds to about 16 hours, alternately from about 1 minute to about 12 hours, from about 20 seconds to about 1 hour, from about 30 seconds to about 8 hours, or from about 45 seconds to about 3 hours.

The term "at least partially chemically and/or physically associates with," which is used herein to describe the interaction of the active agent (and optionally also the solvent/carrier) with the coating layer material and/or surface of the implant, can be defined broadly. Chemical associations, which include various levels of hydrogen-bonding, can range throughout the spectrum from relatively strong associations (e.g., chemical bonds and ionic charge-related attractions/repulsions) to relatively weak associations (e.g., intermolecular interaction based on partial electronic charge distributions, or mild polarity, and secondary intramolecular electronic structure interactions such as alignment of p-orbitals or empty d- or f-orbitals that can lead to intermolecular complexes). Physical associations can also range from relatively strong associations (e.g., co-crystallinity or co-crystallization, entanglements between relatively high molecular weight materials, and high levels of co-alignment or co-orientation) to relatively weak associations (e.g., low levels of co-alignment or co-orientation, van der Waals forces, and alteration of β-, γ-, and/or δ-phase transitions like a glass-amorphous liquid transition in polymers/oligomers such as through plasticization or the like). While certain types of relatively strong interactions between the implant (coating layer) and the active agent and/or active agent solution can be undesirable in circumstances where immediate or relatively quick active agent release in vivo is desired, such strong interactions may be desirable in other circumstances such as where relatively slow or extended/time release in vivo is desired. Thus, the desired release characteristics, as well as the uptake/loading characteristics, of the active agent (and/or solution/carrier) can be controlled by controlling the strength or weakness of the interactions within the system.

Another aspect of the invention relates to the sterile, coated, active agent-loaded implant formed according to the method of the invention described above.

Another aspect of the invention relates to a kit containing (1) a sterile, coated implant formed according to the method of the invention described above and (2) at least one sterile solution/carrier, each containing at least one active agent according to the invention.

In one embodiment of this aspect of the invention, where two or more active agents may be difficult to combine and/or solublize in a single solution/carrier composition, they may be separated into multiple solutions/carriers, such that each solution/carrier composition can contain an individual active agent or a soluble/compatible combination of active agents.

In a preferred embodiment, the kit includes a single solution/carrier containing a solublized/compatible combination of one or more solvents/carriers and the at least one active agent according to the invention.

Another aspect of the present invention relates to a method for in situ treatment of malignant cells from a cancer associated with bone involving: a) treatment of a primary cancer associated with bone, and including positioning an implant according to the invention (i.e., containing and/or coated with an active agent) for treating the malignant cells directly in/on a site containing the malignant cells; and/or b) treatment of a primary cancer associated with bone, and including positioning an implant according to the invention (i.e., containing and/or coated with an active agent) for treating the malignant cells indirectly among/near (e.g., by placing the implant in an area immediately proximal to) a site containing the malignant cells.

As used herein, a cancer that is, or malignant cells that are, "associated with bone" should be understood to include cancers/malignancies of the skeletal system (i.e., bone, marrow, joint and/or vertebral cartilage, cartilagenous fluids, teeth, undifferentiated and/or partially differentiated cells that can differentiate into the preceding, and any combination thereof). In one preferred embodiment, the cancer is or encompasses a bone cancer.

A non-exclusive list of cancers associated with bone include, but are not limited to, osteosarcoma, osteoblastoma, myeloma, multiple myeloma, osteomyeloma, or the like, or a combination thereof. For example, a non-exclusive list of cells that may be malignant and for which treatment according to the invention is warranted includes, but is not limited to, osteoblasts, osteoclasts, cells of the bone corticum, stem cells, marrow cells, cartilage cells, or the like, or a combination thereof.

Another aspect of the present invention relates to a method for in situ treatment of malignant cells from a cancer associated with bone including: a) positioning an implant according to the invention (i.e., containing and/or coated with an active agent) for treating the malignant cells directly in/on a surgical site from which the malignant cells were previously removed/excised; and/or b) positioning an implant according to the invention (i.e., containing and/or coated with an active agent) for treating the malignant cells indirectly among/near (e.g., by placing the implant in an area immediately proximal to) a surgical site from which the malignant cells were previously removed/excised.

In one embodiment according to this aspect of the invention, the implant does not include a hardened bone cement within the bulk of which the at least one active agent is contained. In this embodiment, however, the implant may contain a bone cement, which contains substantially no active agents within its bulk, but which possesses a coating layer containing the at least one active agent. As used herein in reference to one or more compounds, the phrase "contains substantially no" means that there is present not more than about 0.5% by weight, preferably not more than about 0.1% by weight, for example not more than about 0.01% by weight, of the one or more compounds. Additionally or alternately, the phrase "contains substantially no," in reference to one or more compounds, means that there is present an amount of the one or more compounds less than that necessary to have the desired therapeutic effect (e.g., reducing, inhibiting, halting, or reversing the growth of cancer/malignant cells associated with bone), either in vivo or in vitro.

In another embodiment according to this aspect of the invention, the at least one active agent includes a combination of vitamin D (and/or a vitamin D derivative/analog) and a bisphosphonate. However, in an alternate embodiment of the latter method, where the malignant cells are not a result of a primary bone cancer but are instead a result of a metastatic cancer that has spread to bone, the at least one active agent does not include a combination of vitamin D (and/or a vitamin D derivative/analog) and a bisphosphonate.

As used herein, a cancer that is, or malignant cells that are, "associated with bone" should be understood to include cancers/malignancies of the skeletal system (i.e., bone, marrow, joint and/or vertebral cartilage, cartilagenous fluids, teeth, undifferentiated and/or partially differentiated cells that can differentiate into the preceding, and any combination thereof). In one preferred embodiment, the cancer is or encompasses a bone cancer.

A non-exclusive list of cancers associated with bone include, but are not limited to, osteosarcoma, osteoblastoma, myeloma, multiple myeloma, osteomyeloma, or the like, or a combination thereof. For example, a non-exclusive list of cells that may be malignant and for which treatment according to the invention is warranted includes, but is not limited to, osteoblasts, osteoclasts, cells of the bone corticum, stem cells, marrow cells, cartilage cells, or the like, or a combination thereof.

While one or more particular forms of the invention have been illustrated and described, it will also be apparent to those skilled in the art that various modifications can be made without departing from the spirit and scope of the invention.

Each reference cited or referenced herein is hereby incorporated by reference in its entirety herein.

What is claimed is:

1. A medical device for the in situ treatment of malignant cells from a cancer associated with bone, comprising:
    a sterile, coated implant comprising
        an implant defining an outer surface, the implant associated with a bone injury, and the outer surface of the implant being non-porous, non-absorbent in water or an organic liquid, or non-swellable in water or an organic liquid;
        a polymer coating layer at least partially covering the outer surface having an average thickness of at least about 250 microns to about 1000 microns; and
        an active agent suitable for the treatment of the malignant cells, wherein the active agent associates with the polymer coating layer.

2. The medical device of claim 1, wherein the implant outer surface comprises a metal or metal alloy.

3. The medical device of claim 2, wherein the implant is a screw, tack, nail, pin, plate, or rod.

4. The medical device of claim 1, wherein the polymer coating layer is biodegradable.

5. The medical device of claim 1, wherein the polymer coating layer has an average thickness from about 500 microns to about 1 mm.

6. The medical device of claim 5, wherein the thickness of the polymer coating layer is non-uniform across the sterile coated implant.

7. The medical device of claim 1 wherein the polymer coating layer is porous.

8. The medical device of claim 1, wherein the active agent at least partially chemically associates with the polymer coating layer.

9. The medical device of claim 1, wherein the active agent at least partially physically associates with the polymer coating layer.

10. The medical device of claim 8, wherein the active agent at least partially physically associates with the polymer coating layer.

11. The medical device of claim 1, wherein the active agent includes an antibacterial agent, an antiviral agent, an osseointegrative agent, an osteoinductive agent, an osteoconductive agent, or a combination thereof.

12. A medical device kit for the in situ treatment of bone cancer comprising:
    (a) a sterile coated implant having an outer surface wherein a polymer coating layer at least partially covers the outer surface the coating having an average thickness of at least about 250 microns to about 1000 microns, the implant associated with a bone injury;
    wherein the outer surface of the implant is non-porous, non-absorbent in water or an organic liquid, or non-swellable in water or an organic liquid, wherein the sterile coated implant is free of active agent; and (b) a sterile carrier comprising an active agent suitable for the treatment of bone cancer, wherein the sterile carrier is adapted to facilitate at least a partial chemical or physical association, or both, between the active agent and the polymer coating layer.

13. The medical device kit of claim 12, wherein the implant outer surface comprises a metal or metal alloy.

14. The medical device kit of claim 13, wherein the implant is a screw, tack, nail, pin, plate, or rod.

15. The medical device kit of claim 12, wherein the polymer coating layer is biodegradable.

16. The medical device kit of claim 12, wherein the polymer coating layer has a thickness from about 10 nm to about 1 mm.

17. The medical device kit of claim 16, wherein the thickness of the polymer coating layer is non-uniform across the sterile coated implant.

18. The medical device kit of claim 12, wherein the polymer coating layer is porous.

19. The medical device kit of claim 12, wherein the active agent includes an antibacterial agent, an antiviral agent, an osseointegrative agent, an osteoinductive agent, an osteoconductive agent, or a combination thereof.

20. The medical device kit of claim 12, wherein the sterile carrier is adapted to facilitate at least a partial chemical association between the active agent and the polymer coating layer.

* * * * *